United States Patent [19]
Ishikawa et al.

[11] Patent Number: 5,313,950
[45] Date of Patent: May 24, 1994

[54] ULTRASONIC PROBE

[75] Inventors: Hiroshi Ishikawa; Kazuhiro Watanabe; Kenji Kawabe; Takaki Shimura, all of Kawasaki, Japan

[73] Assignee: Fujitsu Limited, Kawasaki, Japan

[21] Appl. No.: 21,228

[22] Filed: Feb. 23, 1993

[30] Foreign Application Priority Data

Feb. 25, 1992 [JP] Japan ................................. 4-38235
Feb. 28, 1992 [JP] Japan ................................. 4-43949

[51] Int. Cl.⁵ .............................................. A61B 8/12
[52] U.S. Cl. ............................ 128/662.06; 128/663.01; 128/662.03
[58] Field of Search .................. 128/662.03, 662.06, 128/663.01, 4; 73/632, 633, 634

[56] References Cited
U.S. PATENT DOCUMENTS

| | | | |
|---|---|---|---|
| 4,408,612 | 10/1983 | Utsugi | 128/662.06 |
| 4,479,388 | 10/1984 | Matzuk | 73/634 |
| 4,880,011 | 11/1989 | Imade et al. | 128/662.06 |
| 5,000,185 | 3/1991 | Yock | 128/662.03 |
| 5,203,338 | 4/1993 | Jang | 128/662.06 |

*Primary Examiner*—William E. Kamm
*Assistant Examiner*—George Manuel
*Attorney, Agent, or Firm*—Staas & Halsey

[57] ABSTRACT

An ultrasonic probe for use in hollow organs such as blood vessels of a living body and in other hollow objects of structures such as pipes, includes a piezoelectric transducer, a reflector and a rotor all housed in a tube. The rotor moves and/or rotates the piezoelectric transducer and/or the reflector and is driven by a stator located outside the object under examination.

13 Claims, 24 Drawing Sheets

FIG. 4A
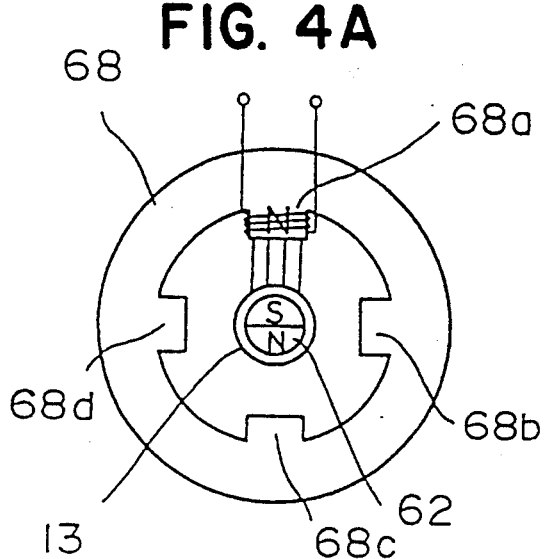
FIG. 4B
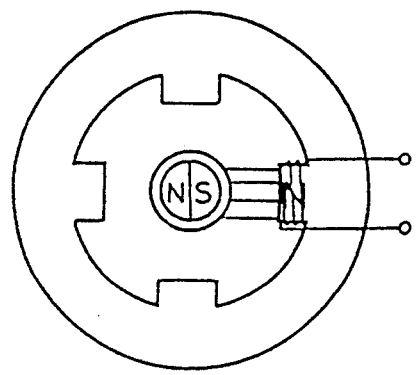
FIG. 4C
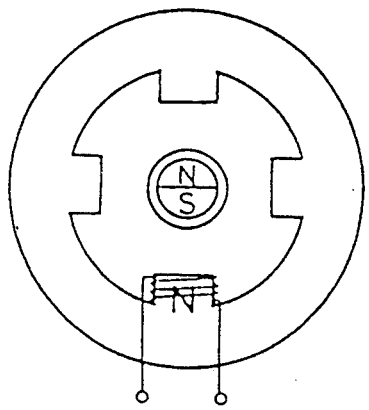
FIG. 4D
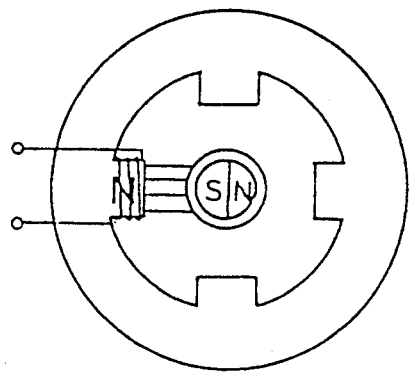
Fig. 4
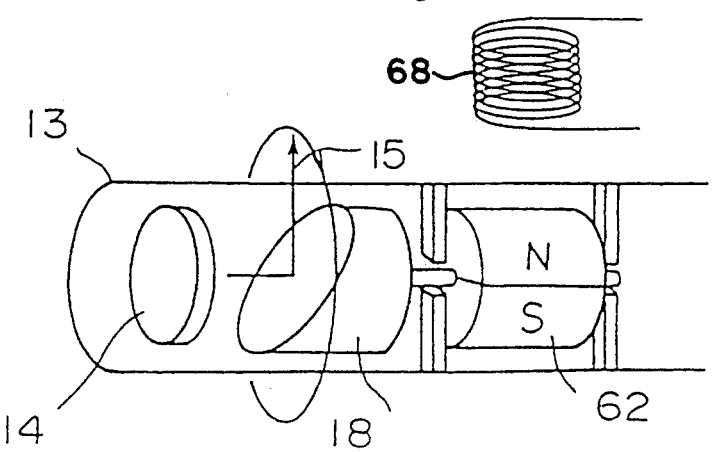
Fig. 5

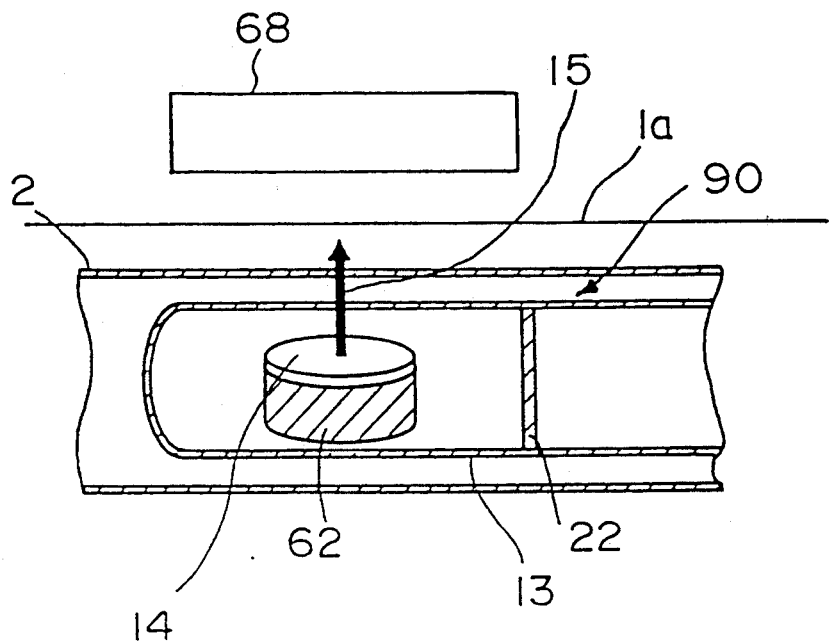
Fig. 16
Fig. 17A
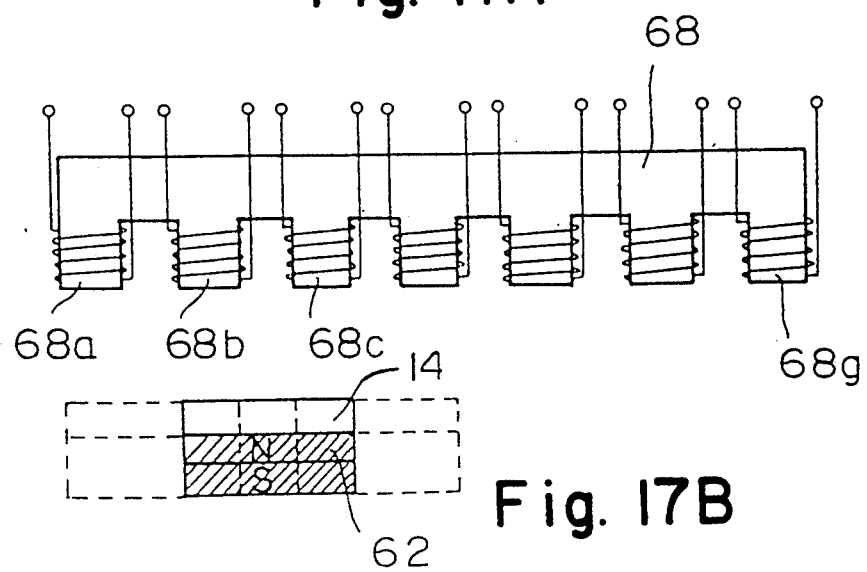
Fig. 17B

ULTRASONIC PROBE

BACKGROUND OF THE INVENTION

1. Field of the Invention

The present invention relates to an ultrasonic probe for probing into hollow objects such as hollow organs of a living body and other hollow constructions. More particularly, the invention relates to an ultrasonic probe having a piezoelectric transducer to be inserted in hollow organs such as the blood vessels of a living body.

2. Description of the Prior Art

There has been a widespread use of ultrasonic diagnostic systems having an ultrasonic probe inserted in blood vessels and other hollow organs of a living body for diagnostic purposes. Hereinafter, the ultrasonic probe inserted in blood vessels is explained. The operating principle of the ultrasonic probe is the same whether it is used in a hollow organs of the human body or in other hollow objects under examination. FIG. 35 is a schematic view showing how an ultrasonic probe is inserted illustratively in blood vessels of a living body. In FIG. 35, the rear end of an ultrasonic probe 12 is connected to an ultrasonic diagnostic system 10. The front end of the probe 12 is inserted from the thigh of a patient 1 into blood vessels before reaching the patient's affected part. The front end of the ultrasonic probe 12 has a piezoelectric transducer that transmits ultrasonic waves and receives their reflection from the affected part. The received signal of the probe 12 is sent to the ultrasonic diagnostic system 10. A monitor screen 11 attached to the system 10 displays an image based on the signal for diagnostic purposes.

FIG. 36 is a schematic view outlining the structure of a typical prior art ultrasonic probe, highlighting the front end thereof (the probe's front end will also be generically called the "ultrasonic probe" hereafter). In FIG. 36, the ultrasonic probe 12 is covered with a tube 13 and tipped with a piezoelectric transducer 14. The piezoelectric transducer 14 is connected to the diagnostic system 10 through lead wires. Opposite to the piezoelectric transducer 14 is a reflector 18 having an oblique reflecting surface 18a.

When a signal is sent from the diagnostic system 10 over the lead wires 16 to the piezoelectric transducer 14, the transducer 14 generates ultrasonic waves 15 toward the reflector 18. The ultrasonic waves are reflected by the reflecting surface 18a of the reflector 18 for transmission into the living body. Tissues in the living body reflect the ultrasonic waves and send them back to the ultrasonic probe 12. The reflected ultrasonic waves are again reflected by the reflecting surface 18a and received by the piezoelectric transducer 14. The received signal of the probe 12 is transmitted to the diagnostic system 10 through the lead wires 16.

One end of a flexible shaft 20 is coupled to the reflector 18. The other end of the flexible shaft 20 is connected to the shaft of a motor 25 incorporated in the diagnostic system 10. As the motor 25 rotates, the torque is transmitted to the reflector 18 via the flexible shaft 20, thus rotating the reflector 18. This allows the ultrasonic waves from the piezoelectric transducer 12 to probe the blood vessel circumferentially, producing a sectional view of the blood vessel under examination.

In the rear of the reflector 18 is a partition plate 22 that seals the front end of the probe from the rest. The sealed space is filled with acoustic coupling substance, for example physiological salt water, of which the acoustic impedance is approximately the same as that of the living body.

FIG. 37 is a schematic view of another prior art ultrasonic probe. In this figure and other figures that follow, those component parts having the same functions as their counterparts in FIG. 36 are designated by like reference numerals regardless of their differences in specific constructions. Descriptions of these parts will be omitted if they are repetitive, and only the significant differences therebetween will be described. In the example of FIG. 37, a motor 32 for rotating the reflector 18 is built in an ultrasonic probe 30. The motor 32 is connected to the diagnostic system 10 through the lead wires 34.

FIGS. 38 and 39 are schematic views of other prior art ultrasonic probes. The ultrasonic probe 40 of FIG. 38 has the piezoelectric transducer 14 fixed crosswise with respect to a flexible shaft 42. Moving the flexible shaft 42 lengthwise causes ultrasonic waves 15 to scan linearly the object under examination. The ultrasonic probe 50 of FIG. 39 is also used for linear scanning. In this construction, the piezoelectric transducer 14 is fixed to a rotor 52 of a linear motor. The stator 54 of the linear motor is secured to the inner wall of the tube 13.

Of these prior art ultrasonic probes outlined above, those in FIGS. 36 and 38 using the flexible shaft or the like to rotate or move the reflector or piezoelectric transducer have a major disadvantage. That is, the relative rigidity of the flexible shaft or its equivalent detracts from the flexibility of the ultrasonic probe as a whole. This makes it difficult for the probe operator to insert the ultrasonic probe illustratively into bent blood vessels in order to reach the affected part of the living body.

The prior art ultrasonic probes shown in FIGS. 37 and 39 contain a motor inside and thus do away with the flexible shaft. Removing the flexible shaft or its equivalent ensures good flexibility and operability of the ultrasonic probe. However, with the motor incorporated inside, ultrasonic probes of this kind necessarily have greater outer diameters. The enlarged outer diameter makes it impossible to insert the probe in fine blood vessels and similar hollow objects.

SUMMARY OF THE INVENTION

It is therefore an object of the present invention to overcome the above-described drawbacks and disadvantages of the prior art and to provide an ultrasonic probe that is flexible and is small in outer diameter.

In carrying out the invention and according to one aspect thereof, there is provided an ultrasonic probe comprising: a tube extending in a predetermined direction for insertion into an object under examination; and a transmitter-receiver disposed so that at least a part thereof is capable of at least one of two movements, one movement being in a predetermined direction, the other movement being rotary around an axis coinciding with the predetermined direction, the transmitter-receiver transmitting ultrasonic waves into the object under examination and receiving the waves reflected by the object under examination; wherein the tube incorporates a rotor causing at least part of the transmitter-receiver to perform at least one of the two movements, the rotor being driven externally by a stator located outside the object under examination.

In a preferred structure according to the invention, at least a part of the rotor is made of a magnetic substance or a permanent magnet. With this structure, where the transmitter-receiver comprises a piezoelectric transducer that performs at least one of the two movements, the rotor having a magnetic substance or a permanent magnet is preferably attached to the piezoelectric transducer. The piezoelectric transducer is attached preferably to the front end of the rotating shaft of the rotor. As an alternative, the piezoelectric transducer is attached preferably to a lateral position of the rotating shaft of the rotor. Moreover, the rotor is preferably shaped into a cylinder.

In another preferred structure according to the invention, the transmitter-receiver comprises a piezoelectric transducer and a reflector. The piezoelectric transducer transmits and receives ultrasonic waves. The reflector reflects toward outside the tube the ultrasonic waves emitted by the piezoelectric transducer, and reflects again the waves returned from outside the tube toward the piezoelectric transducer. The reflector preferably has the magnetic substance or permanent magnet used as the rotor when the reflector performs one of the two movements.

As an alternative to this structure, the tip of the tube is provided preferably with a hollow chamber filled with an acoustic coupling substance. A rotor-equipped reflector is inserted into the chamber. The entrance to the chamber is capped with the piezoelectric transducer. As another alternative, the tip of the tube is provided with a hollow chamber. The deep end of the chamber is capped with the piezoelectric transducer. The space inside the chamber is filled with an acoustic coupling substance. The tip side of the chamber is provided with a rotor-equipped reflector, the tip being closed with a cap.

In yet another preferred structure according to the invention, the stator preferably has a handle. As an alternative, the stator is preferably equipped with an articulated arm mechanism. As another alternative, the stator preferably has a soft body furnished on its surface that comes into contact with the object under examination.

The invented ultrasonic probe contains in its tube the rotor for moving or rotating at least part of its components such as the piezoelectric transducer or the reflector, the rotor being driven by the stator located outside the living body under examination. By eliminating the need for a conventional flexible shaft or its equivalent, the structure ensures the flexibility of the probe. With the stator located outside the tube, the outer diameter of the tube is made substantially small.

As mentioned earlier, the prior art ultrasonic probe is filled at least partially with physiological salt water or its equivalent. With electrical signals to the piezoelectric transducer sent in pulses, the transducer need not be powered constantly and the lead wires connected thereto are generally made waterproof.

However, the rotor inside the ultrasonic probe needs to be powered constantly. This means that with prior art probes, there is a possibility—although remote—that the salt water may leak and cause electric shock to the patient being examined.

By contrast, where the rotor is made of a magnetic substance or a permanent magnet, as in the novel ultrasonic probe according to the invention, there is no possibility of electric shock to the patient. With that ultrasonic probe, the magnetic substance or permanent magnet used as the rotor is fixed directly to the piezoelectric transducer. Alternatively, the reflector is composed of the magnetic substance or permanent magnet, and the assembly as a whole is used as the rotor. This eliminates the need for a separate rotor, making it possible to constitute an ultrasonic probe with an even smaller outer diameter.

Where the magnetic substance or permanent magnet used as the rotor is shaped in the form of a cylinder, a laser fiber or like therapeutic means may be passed therethrough. Doctors may treat the patient's affected part through observation with an ultrasonic probe of this kind.

Where the piezoelectric transducer is attached to the front end of the rotating shaft of the rotor, rotating the rotor provides an ultrasonic image of the portion in front of the probe. For example, even if the blood vessel under examination is clogged with lipid, the thickness of the occlusion and other related aspects of the affected part may be observed with the ultrasonic probe.

Where the piezoelectric transducer is attached to a lateral position of the rotating shaft of the rotor, rotating the rotor provides a sectional image perpendicular to the rotating shaft. If a donut-shaped piezoelectric transducer is attached to the front end of the rotating shaft of the rotor, it is possible to acquire a sectional image which reflects an affected part in front of the rotating shaft and which perpendicularly intersects a rotating shaft extension.

Since the stator is located outside the object under examination, furnishing the stator with a handle or with an articulated arm mechanism enhances its operability. Where the stator is equipped with a soft body on its surface that comes into contact with the object under examination, the stator feels good upon contacting the object through improved snugness therebetween.

These and other objects, features and advantages of the invention will become more apparent upon a reading of the following description and appended drawings.

BRIEF DESCRIPTION OF THE DRAWINGS

FIGS. 4A, B, and D are a set of schematic views depicting a typical rotor-stator construction wherein the rotor is made of a permanent magnet in connection with the first embodiment;

FIG. 5 is a schematic view of another motor wherein the rotor is made of a permanent magnet in connection with the first embodiment;

FIG. 16 is a schematic view of an ultrasonic probe according to a sixth embodiment of the invention;

FIGS. 17A and 17B are views illustrating the operating principle of a linear motor composed of a rotor 62 and a stator 68 in the sixth embodiment of FIG. 16;

DESCRIPTION OF THE PREFERRED EMBODIMENTS

Figure 1:
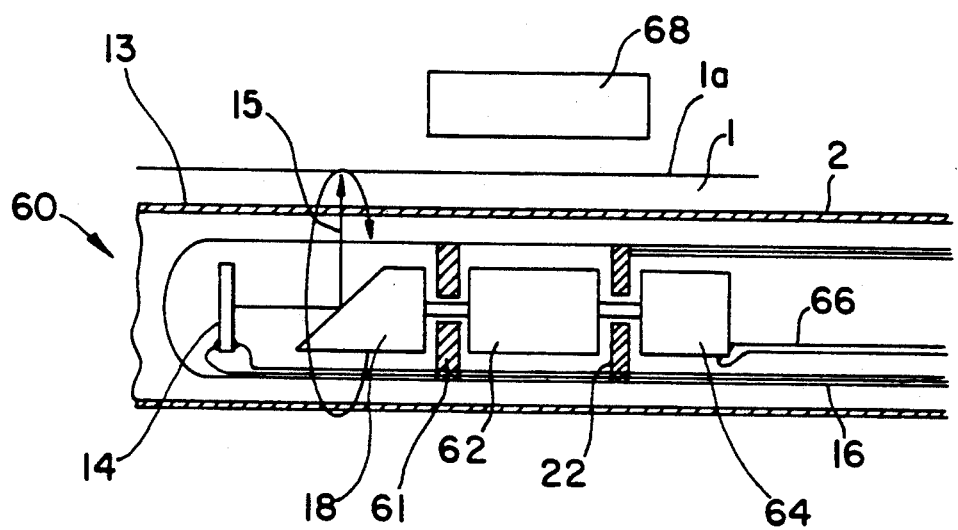
FIG. 1 is a schematic view of an ultrasonic probe according to a first embodiment of the invention.

The preferred embodiments of the invention will now be described in detail. In describing the embodiments, the parts that are functionally identical to those already described in connection with the prior art examples (FIGS. 35 through 39) are designated by like reference numerals regardless of their differences in specific constructions. Descriptions of these parts will be omitted if they are repetitive.

FIG. 1 shows schematically an ultrasonic probe 60 according to the first embodiment of the invention. In FIG. 1, a reflector 18 is connected through a bearing 61 to a rotor 62 that constitutes part of a motor. The rotor 62 is connected to a detector 64 through a partition plate 22 that doubles as a bearing, the detector 64 detecting the revolutions of the rotor 62. The rotating speed of the rotor 62 detected by the detector 64 is transmitted via lead wires 66 to a diagnostic system 10.

Outside the body surface 1a of a patient 1 is a stator 68 that drives the rotor 62. In this embodiment, the rotor 62 is made of a magnetic substance. It should be noted that FIG. 1 takes liberties with the depth between the body surface and the blood vessel (i.e., shown shallower than is actually the case) in order to highlight the operating principle of the embodiment.

Figure 2:
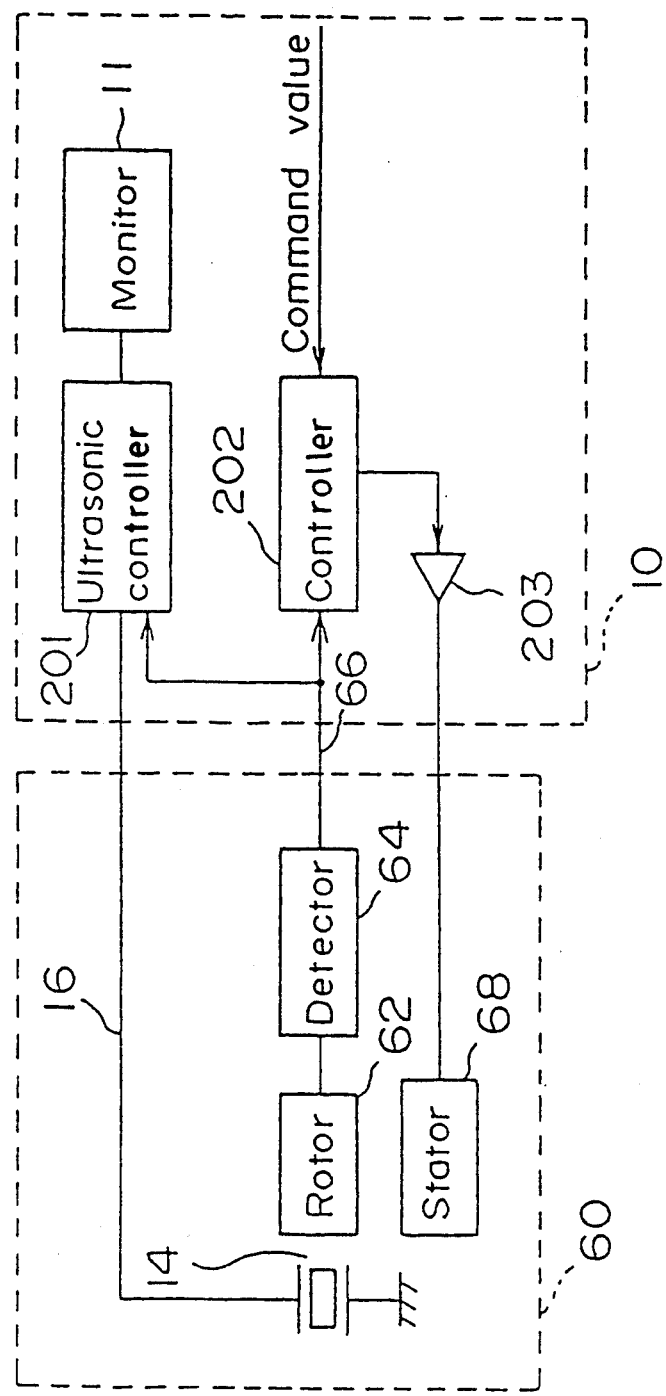
FIG. 2 is a schematic block diagram of an ultrasonic diagnostic system equipped with the first embodiment of FIG. 1.

FIG. 2 is a schematic block diagram of an ultrasonic diagnostic system equipped with the first embodiment of FIG. 1. The diagnostic system 10 (see FIG. 35) incorporates an ultrasonic controller 201 containing a piezoelectric transducer driving circuit, a received signal processing circuit and other components. The ultrasonic controller 201 sends an ultrasonic emission signal through lead wires 16 to a piezoelectric transducer 14 in an ultrasonic probe 60. In turn, the piezoelectric transducer 14 emits ultrasonic waves into the living organ under examination. The reflected ultrasonic waves from the tissues of the organ are received by the piezoelectric transducer 14, and the received signal is sent through the lead wires 16 back to the ultrasonic controller 201.

The diagnostic system 10 also has a controller 202 for controlling the rotor 62 and stator 68 which make up the motor. Given appropriate commands, the controller 202 drives the stator 68 through an amplifier 203 so that a necessary magnetic field will be generated around the rotor 62. The detector 64 detects the rotating speed of the rotor 62. A signal representing the rotating speed is transmitted to the controller 202 via the lead wires 66. The controller 202 compares the transmitted rotating speed with a reference command value. Another signal representing the position of the rotor 62 detected by the detector 64 is input to the ultrasonic controller 201 along with the electric signal denoting the reflected ultrasonic waves. The ultrasonic controller 201 processes the input signals and supplies a monitor 11 with a signal reflecting the result of the processing. Based on the signal received, the monitor 11 displays a sectional image showing a circumferential view of the blood vessel under examination.

From the block diagram of FIG. 2 and the above description in connection therewith, it is easy to devise by analogy basic system circuit arrangements for linear and sector scans, among others. Appropriate identification signals from the ultrasonic probe help to implement diverse scanning methods including radial scan for obtaining circumferential views of blood vessels, linear scans and sector scans. The processing of the signals specific to each scanning method is performed with known techniques in conjunction with ultrasonic diagnostics.

Figure 3C:
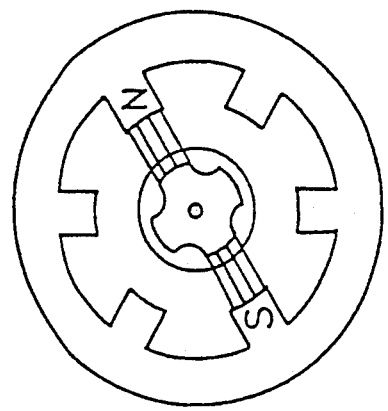
FIGS. 3A, b, and c are a set of schematic views showing a typical motor construction made of a rotor and a stator in connection with the first embodiment.
Figure 3B:
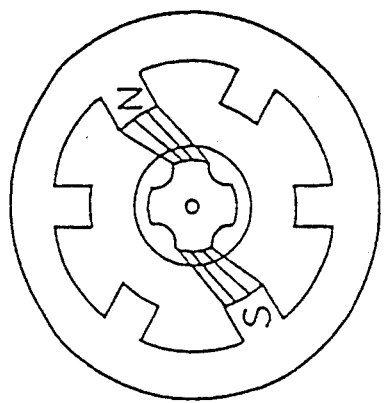
Figure 3A:
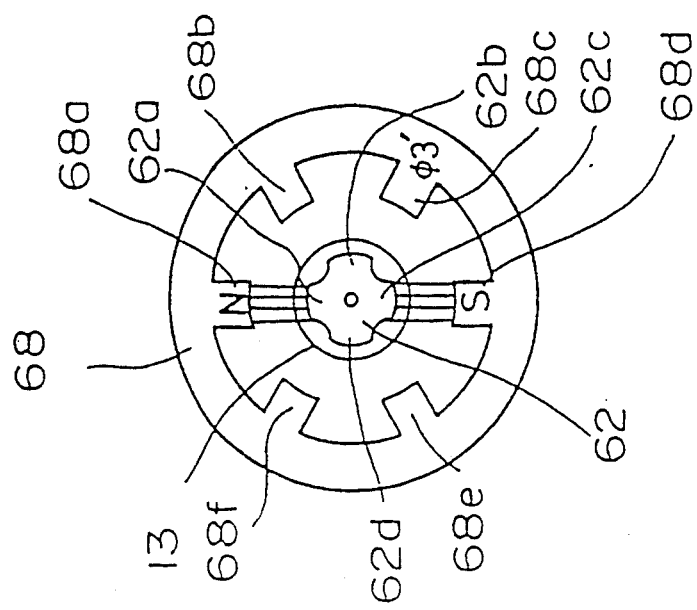

FIGS. 3A-3B offer a set of schematic views showing a typical motor construction made of a rotor and a stator in connection with the first embodiment. As illustrated, a tube 13 contains the rotor 62 made of a magnetic substance, the rotor having four projections 62a through 62d. The stator 68 is shaped substantially as a hollow cylinder having six projections 68a through 68f. The stator 68 is large enough to accommodate within its hollow interior a human body to be examined.

Suppose that the projections 68a and 68d of the stator 68 are excited to become an N and an S pole, respectively, and that the projections 62a and 62c of the rotor 62 are positioned opposite to the projections 68a and 68d of the stator 68, respectively, as shown in FIG. 3(A). In this state, removing the excitement of the projections 68a and 68d and exciting the projections 68b and 68e to become an N and an S pole exerts a counterclockwise torque to the rotor 62 according to the Maxwell stress principle. The rotor 62 thus turn counterclockwise, reaching the state of FIG. 3(C). Switching the excited projections in turn causes the rotor 62 to rotate. Although the stator 68 is a six-pole type and the rotor 62 a four-pole type in this example, the number of poles for either component is obviously not limited thereto.

FIGS. 4A-4B are a set of schematic views depicting a typical rotor-stator construction wherein the rotor is made of a permanent magnet. In this example, the stator 68 has four projections 68a through 68d. The rotor 62 made of the permanent magnet has no projections. In operation, the projections 68a through 68d of the stator 68 are excited in that order to become an N pole one at a time, as shown in FIGS. 4(A) through 4(D). This causes the rotor 62 to rotate clockwise. Although the stator 68 is a four-pole type and the rotor 62 a two-pole type in this example, the number of poles for either component is obviously not limited thereto. For example, the stator 68 may be a six-pole type and the rotor 62 a four-pole type.

FIG. 5 schematically depicts another motor wherein the rotor is made of a permanent magnet. This example includes a coil-clad stator 68. When an AC current changing sinusoidally is made to flow through the coil, the rotor side of the coil generates an N and an S pole alternately. This causes the rotor 62 to rotate.

Figure 6:
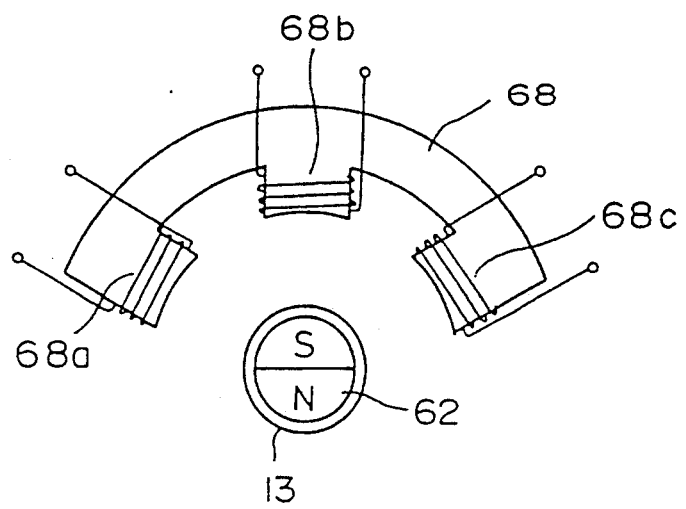
FIG. 6 is a schematic view of yet another motor wherein the rotor is made of a permanent magnet in connection with the first embodiment.

FIG. 6 schematically shows yet another motor wherein the rotor is made of a permanent magnet. As opposed to the stator constructions of FIGS. 3 and 4 wherein the stator surrounds the patient's body, the example of FIG. 6 has a circular arc type stator. In operation, the stator 68 is first excited so that its projection 68a develops an N pole. This causes the S pole of the rotor 62 to be attracted to the projection 68a. The stator 68 is then excited so that its projection 68c develops an S pole. This causes the N pole of the rotor 62 to be attracted to the projection 68c. Thereafter, the rotor 62 rotates counterclockwise as the excitement is shifted as follows: projection 68b (S pole), projection 68a (S pole), projection 68c (N pole), projection 68b (N pole), projection 68a (N pole), projection 68c (S pole) and projection 68b (S pole), in that order.

The example of FIG. 6 is noted for its superior operability thanks to the circular arc type stator employed. It is also possible to install a plurality of circular arc type stators with the patient's body taken as the approximate center of these stators.

As described, diverse constructions are feasible when the rotor 62 in the ultrasonic probe is made of a magnetic substance or permanent magnet, with the stator 68 located outside the patient's body to drive the rotor 62 therefrom.

Figure 7:
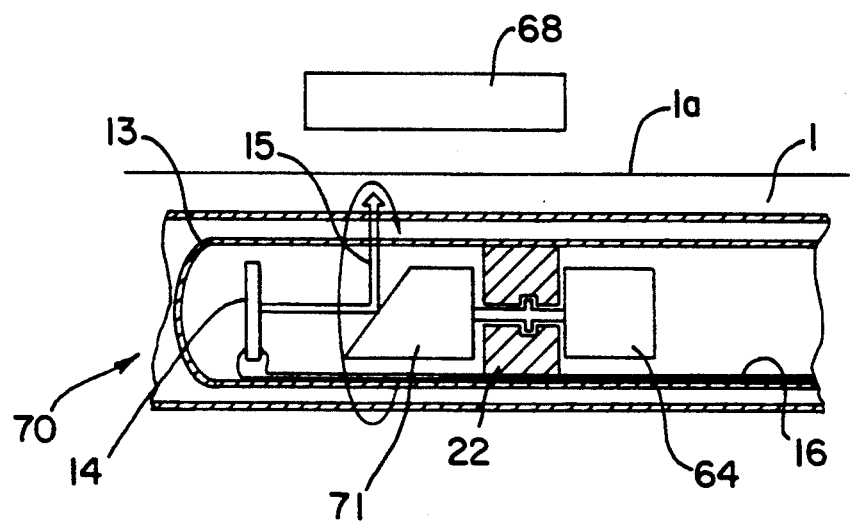
FIG. 7 is a schematic view of an ultrasonic probe according to a second embodiment of the invention.

FIG. 7 schematically shows an ultrasonic probe according to a second embodiment of the invention. In FIG. 7, an ultrasonic probe 70 comprises a reflector 71 made of a magnetic substance or permanent magnet. The reflector 71 is connected to a detector 64 through a partition plate 22 that doubles as a bearing. In this manner, the reflector may constitute a rotor.

Figure 8:
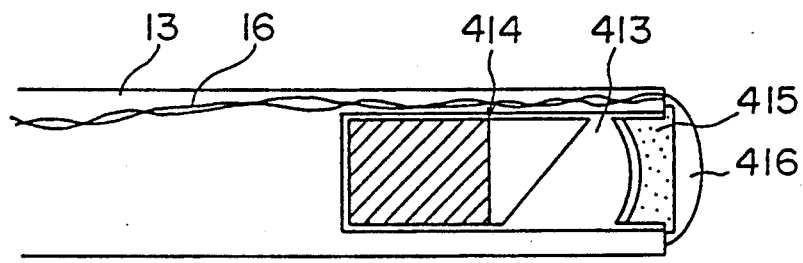
FIG. 8 is a schematic view of an ultrasonic probe according to a the third embodiment of the invention.
Figure 9:
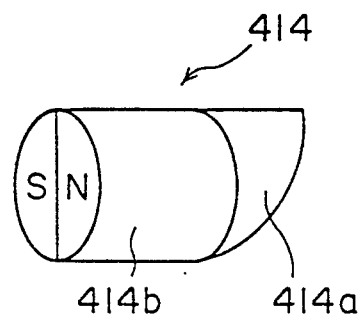
FIG. 9 is a schematic view of a rotor-equipped reflector constituting part of the third embodiment shown in FIG. 8.
Figures 10A, 10B:
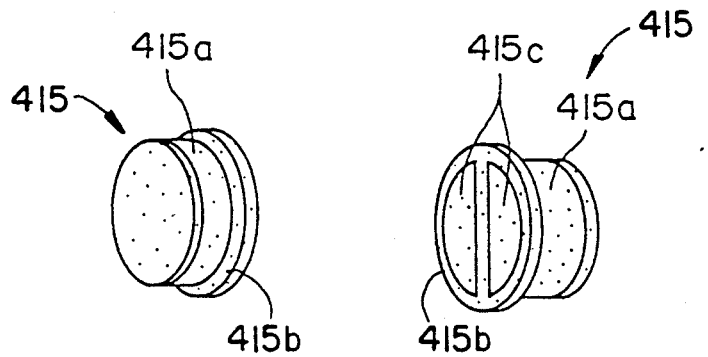
FIGS. 10A and 10B are a set of perspective views showing from different angles a flange-equipped piezoelectric transducer constituting part of the third embodiment shown in FIG. 8.

FIG. 8 is a schematic view of an ultrasonic probe according to a third embodiment of the invention. FIG. 9 is a schematic view of a rotor-equipped reflector constituting part of the third embodiment in FIG. 8. FIGS. 10A and 10B are a set of perspective views showing from different angles a flange-equipped piezoelectric transducer constituting part of the third embodiment in FIG. 8.

The tip of the tube 13 is provided with a hollow chamber 413. At the back of the hollow chamber 413 is provided a rotor-equipped reflector 414. As depicted in FIG. 9, the reflector 414 comprises a mirror part 414a reflecting ultrasonic waves and a rotor 414b made of a permanent magnet.

The space inside the hollow chamber 413 is filled with an acoustic coupling substance such as physiological saltwater. At the tip of the chamber 413 is provided a piezoelectric transducer 415. As illustrated in FIGS. 10A and 10B, the outer circumference of the piezoelectric transducer 415 is covered with a sealing material 415a. A flange 415b is attached to an edge of the piezoelectric transducer 415. The hollow chamber 413 is capped with the piezoelectric transducer 415 whose structure is shown in FIGS. 10A and 10B. The piezoelectric transducer 415 used as the cap shields the hollow chamber 413 from the outside. At the tip of the tube 13 is the sealing material covering the piezoelectric transducer 415. The sealing material keeps the hollow chamber 413 completely watertight. The lead wires 16 are connected to electrodes 415c (see FIG. 10B) of the piezoelectric transducer 415.

The piezoelectric transducer of the structure shown in FIG. 8 is assembled as follows. The rotor-equipped reflector 414 is first inserted in the hollow chamber 413. The chamber 413 is then filled with the acoustic coupling substance. After this, the chamber 413 is capped with the piezoelectric transducer 415. The tip of the tube 13 is covered with the sealing material 416 such as silicon rubber.

Figure 11:
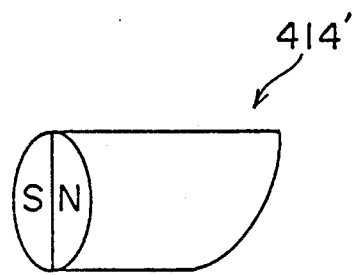
FIG. 11 is a view of showing an alternative reflector that may be used in place of the reflector of FIG. 9 in the third embodiment of FIG. 8.

FIG. 11 is a view showing an alternative reflector 414' that may be used in place of the reflector 414 of FIG. 9 in the third embodiment of FIG. 8. The reflector 414' may be composed entirely of a permanent magnet that includes the portion corresponding to the mirror part 414a of the reflector in FIG. 9. The rotor-equipped reflector 414' is manufactured by cutting an appropriate piece of permanent magnet obliquely.

Figure 12:
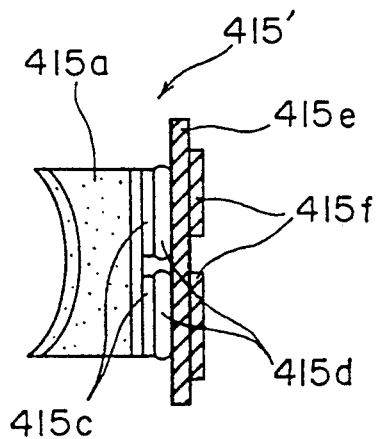
FIG. 12 is a view depicting a piezoelectric transducer that may be used in place of the piezoelectric transducer in FIG. 10 for use with the third embodiment of FIG. 8.

FIG. 12 is a view depicting a piezoelectric transducer 415' that may be used in place of the piezoelectric transducer 415 in FIGS. 10A and 10B for use with the third embodiment of FIG. 8. The piezoelectric transducer 415' of FIG. 12 has its electrodes 415c coupled to a circuit board 415e by solder parts 415d, the circuit board 415e by solder parts 415d, the circuit board 415e incorporating circuit devices 415f constituting an ultrasonic wave receiving circuit. The circuit board 415e plays the role of a flange 415b attached to the piezoelectric transducer 415 of FIG. 9. Placing the circuit board 415e together with its ultrasonic wave receiving circuit into the piezoelectric transducer as shown in FIG. 12 reduces the size of the ultrasonic probe as a whole and contributes to reduction of the noise involved. Where the flange is made of the circuit board 415e itself, there is no need to equip the circuit board with an additional flange. This aspect of the structure also contributes to reduction of the probe size. Although the embodiments that follow do not refer specifically to the use of a flange or ultrasonic wave receiving circuit with the piezoelectric transducer, these attachments may be provided where necessary in the same manner as with the embodiment depicted in FIGS. 8 through 12.

Figure 13:
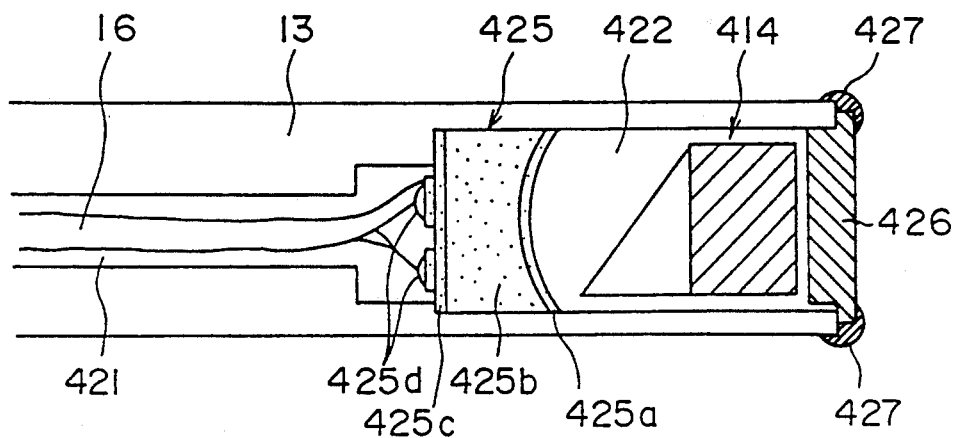
FIG. 13 is a schematic view of an ultrasonic probe according to a fourth embodiment of the invention.

FIG. 13 is a schematic view of an ultrasonic probe of a fourth embodiment of the invention.

Figure 14:
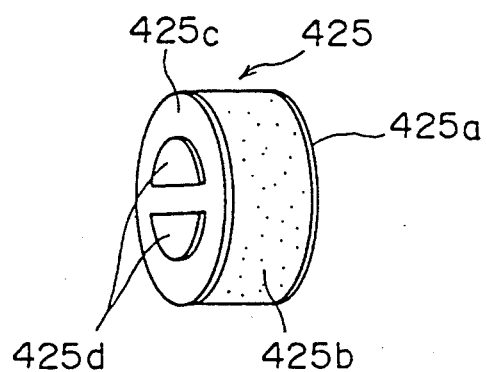
FIG. 14 is a perspective view of a piezoelectric transducer for use with the fourth embodiment of FIG. 13.

FIG. 14 is a perspective view of a piezoelectric transducer for use with the fourth embodiment of FIG. 13.

Inside the tube 13 constituting part of the fourth embodiment is a hole 421 through which the lead wires 16 are passed. The tip of the tube 13 is equipped with a hollow chamber 422 that is larger than the hole 421 in inner diameter. At the deep end of the hollow chamber 422 is a piezoelectric transducer 425. As shown in FIG. 14, the piezoelectric transducer 425 comprises a concave piezoelectric part 425a, a backing part 425b attached to the back of the piezoelectric part 425a, and a substrate 425c having electrodes 425d and attached to the back of the backing part 425b. The piezoelectric transducer 425 of this structure is disposed at the deep end of the hollow chamber 422, thereby shielding the chamber 422 from the hole 421. The hollow chamber 422 is filled with an acoustic coupling substance. Inside the hollow chamber 422 and opposite to the piezoelectric transducer 425 is a rotor-equipped reflector 414 such as the one shown in FIG. 9. The tip of the hollow chamber 422 is capped with a lid 426. The circumference of the lid 426 is covered with a sealing material 427 such as silicon rubber, which keeps the chamber 422 watertight.

The ultrasonic probe whose structure is depicted in FIG. 13 is assembled as follows. The piezoelectric transducer 425 is first inserted from the tip of the tube 13. The transducer 425 shields the hollow chamber 422 from the hole 421 through which the lead wires 16 are passed. Then the rotor-equipped reflector 414 is disposed inside the hollow chamber 422 which is thereupon filled with the acoustic coupling substance. After this, the tip of the tube 13 is capped with the lid 426. The circumference of the lid 426 is covered with the sealing material 427. With the fourth embodiment, the piezoelectric transducer 425 is located at the deep end of the hollow chamber 442, and the electrodes 425d at the back of the transducer 425 are connected to the lead wires 16. This setup, in which the lead wires 16 need only be passed through the hole 421, further facilitates the assembly of the ultrasonic probe.

Figure 15:
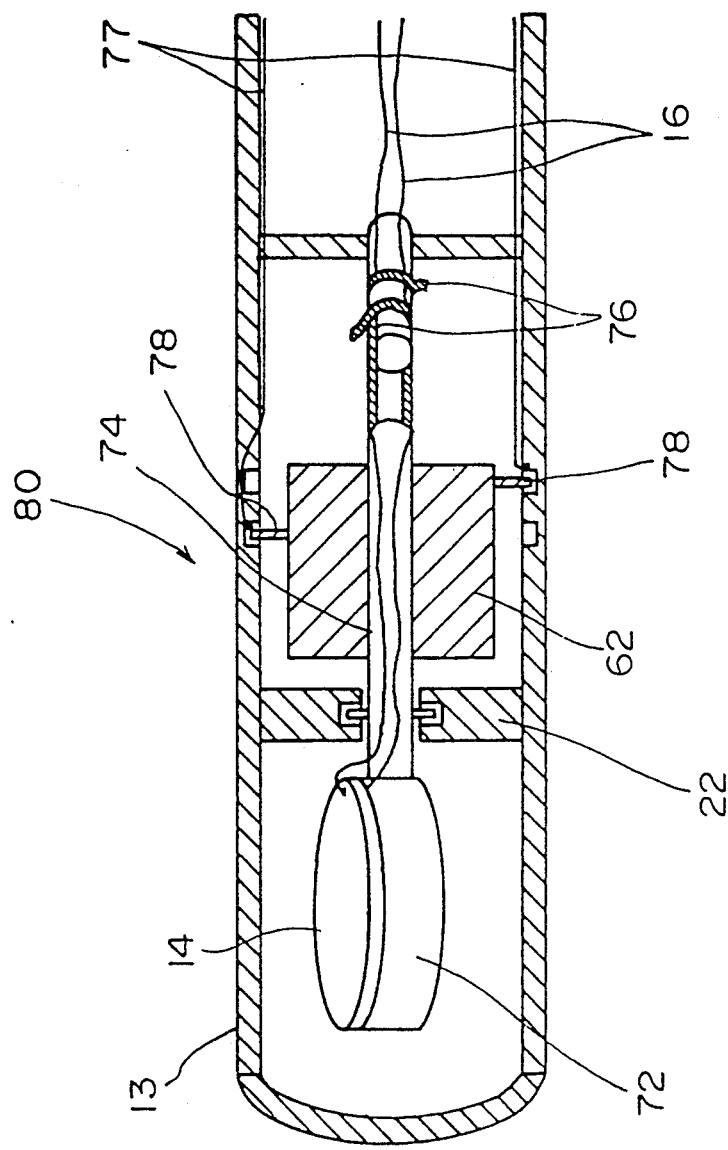
FIG. 15 is a schematic view of an ultrasonic probe according to a fifth embodiment of the invention.

FIG. 15 is a schematic view of an ultrasonic probe of a fifth embodiment of the invention. In FIG. 15, an ultrasonic probe 80 has no reflector. A piezoelectric transducer 14, disposed crosswise, emits ultrasonic waves direct in the lateral direction. The back of the piezoelectric transducer 14 has a backing 72 attached thereto for absorbing the ultrasonic waves emitted from the back. The backing 72 is fixed to a rotating shaft 74. To this rotating assembly, a rotor 62 is attached securely. Lead wires 16 are connected to the piezoelectric transducer 14 via a brush 76 and through the interior of the rotating shaft 74. The rotor 62 made of an electromagnet is connected to the diagnostic system 10 (see FIG. 35) via lead wires 77 and a brush 78.

As the fifth embodiment indicates, it is possible to let the piezoelectric transducer 14 rotate. In this case, the rotor 62 is made of the electromagnet. Alternatively, the rotor 62 may be constituted by a permanent magnet or by a magnetic substance.

FIG. 16 schematically depicts an ultrasonic probe of a sixth embodiment of the invention. In FIG. 16, an ultrasonic probe 90 has a rotor 62 attached to the back of a piezoelectric transducer 14, the rotor being made of a magnetic substance or permanent magnet. The rotor 62 and a stator 68 combine to make up a linear motor. The linear motor moves the piezoelectric transducer 14 inside and in parallel with a tube 13, thus performing linear scanning based on ultrasonic waves 15.

FIGS. 17A and 17B illustrate the operating principle of a linear motor composed of the rotor 62 and stator 68 in the sixth embodiment of FIG. 16. In operation, the rotor 68 is first positioned opposite to the projections 68a and 68b of the stator 68, and the projections 68a and 68b are excited so that they develop an S pole each. Thereafter, the projections are excited two at a time so that they develop an S pole in turn (68b and 68c, 68c and 68d, . . . , 68f and 68g). This causes the piezoelectric transducer 14 to move horizontally, allowing linear scanning to take place.

Figure 18:
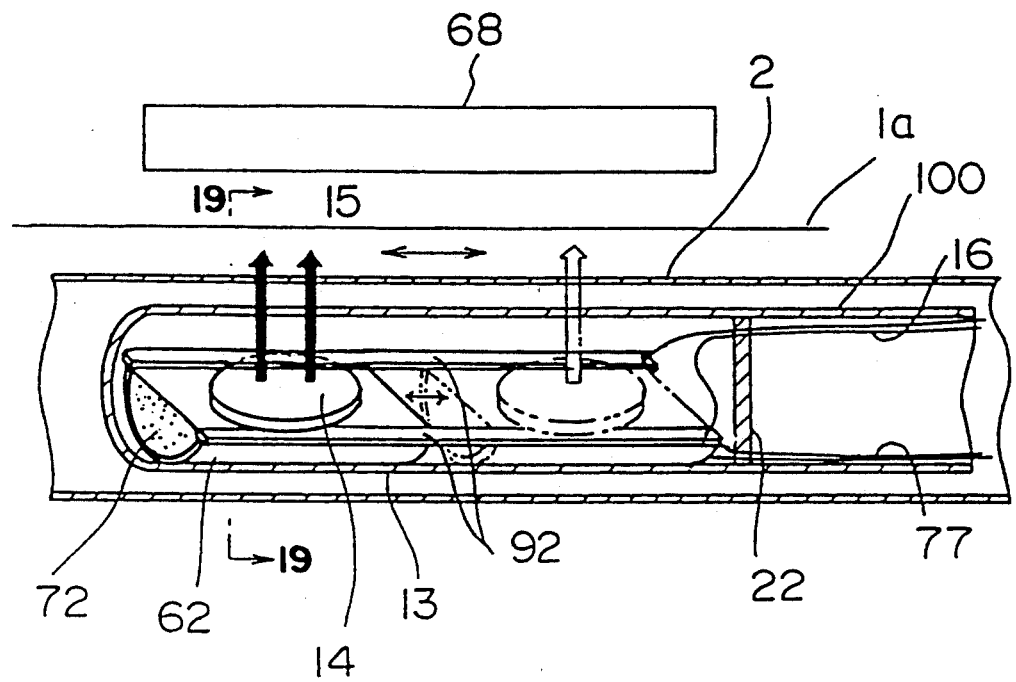
FIG. 18 is a schematic view of an ultrasonic probe according to a seventh embodiment of the invention.
Figure 19:
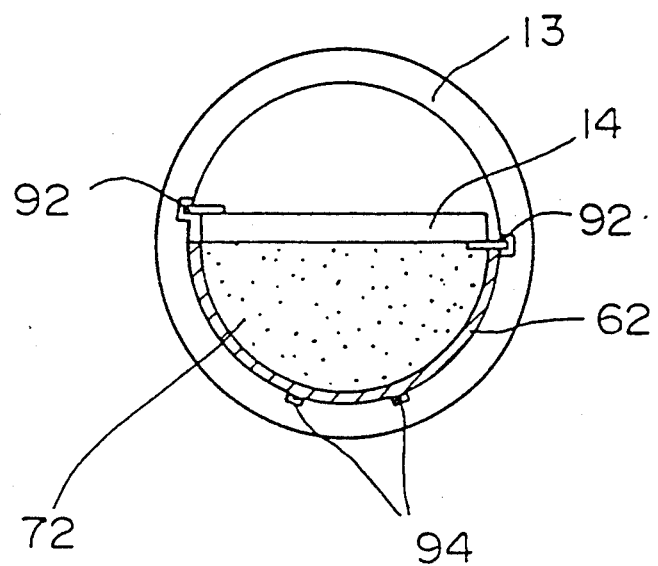
FIG. 19 is a sectional view taken on line X—X in FIG. 18.

FIG. 18 schematically depicts an ultrasonic probe of a seventh embodiment of the invention, and FIG. 19 is a sectional view taken on line X—X in FIG. 18. As shown in FIG. 19, the back of a piezoelectric transducer 14 has a semi-cylindrical backing 72 attached thereto. A rotor 62 is formed along the backing 72. With this embodiment, the rotor 62 is made of an electromagnet and, in combination with a stator 68, constitutes a linear motor. The piezoelectric transducer 14 is connected to lead wires 16 via a brush 92, as shown in FIG. 18. The rotor 62 is powered with a brush 94 via lead wires 77. Although the rotor 62 of this embodiment comprises an electromagnet, the rotor may utilize a permanent magnet instead. The workings of the piezoelectric transducer 14 of the seventh embodiment are the same as those of the sixth embodiment in FIG. 16.

Figure 20:
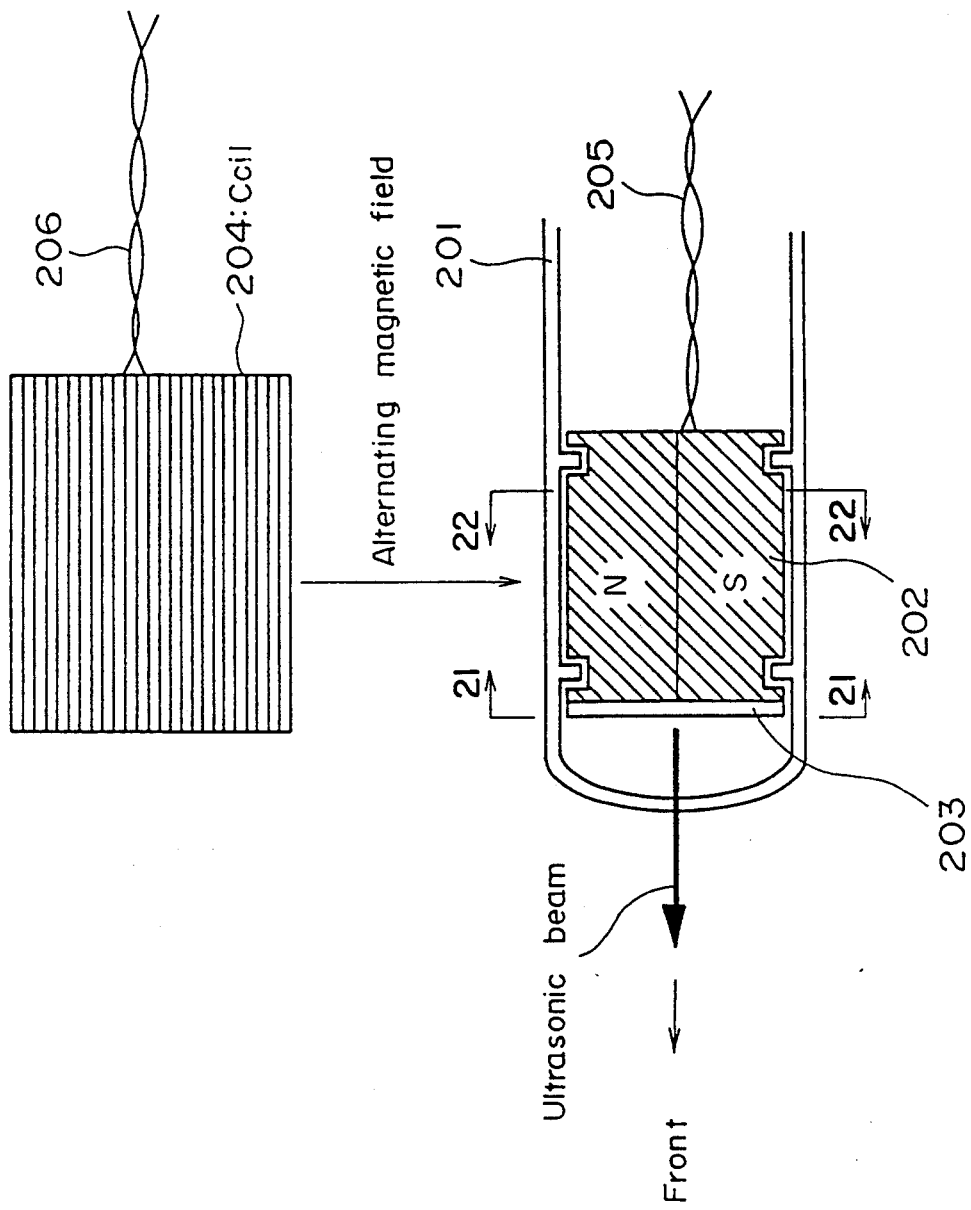
FIG. 20 is a sectional view of an ultrasonic probe according to an eighth embodiment of the invention.
Figure 21:
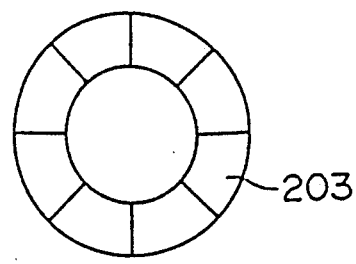
FIG. 21 is a sectional view taken on line X—X in FIG. 20.
Figure 22:
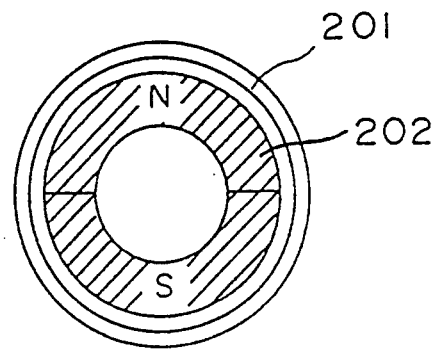
FIG. 22 is a sectional view taken on line Y—Y in FIG. 20.

FIG. 20 is a sectional view of an ultrasonic probe of an eighth embodiment of the invention. FIG. 21 is a sectional view taken on line X—X in FIG. 20, and FIG. 22 is a sectional view taken on line Y—Y in FIG. 20. In FIG. 20, a tube 201 is led in continuously from outside the patient's body. It is through the tube 201 that the ultrasonic probe is inserted and extracted to and from the body. A cylindrical permanent magnet 202 is a rotor that makes up part of a motor. The magnet 202 is split in two, constituting a two-pole type motor as depicted in FIG. 22. And as shown in FIG. 20, the permanent magnet 202 has two grooves in alignment with two circumferential rings inside the tube 201; the grooves and rings are engaged rotatably with one another.

A donut-shaped piezoelectric transducer 203 is attached to the front end of the cylindrical permanent magnet 202, as illustrated in detail in FIG. 21. The piezoelectric transducer 203 is divided into eight parts. This construction, intended to enhance the frame rate, is a sort of synthetic aperture construction that acquires a three-dimensional structural view of an object ahead.

A coil 204 generates an alternating magnetic field when supplied with currents from lead wires 206. The coil 204 and the permanent magnet 202 making up part of the rotor combine to constitute a motor. This motor may be a Hall motor using a Hall-effect device for detecting the rotor position. Lead wires 205 apply voltages to the electrodes of the piezoelectric transducer 203.

Figure 23:
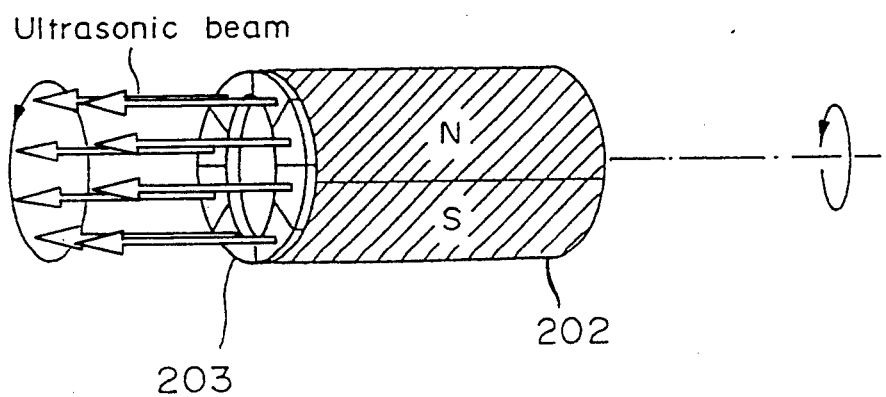
FIG. 23 is a view illustrating how the eighth embodiment performs its ultrasonic scanning.

How some of the embodiments work will now be described. FIG. 23 illustrates how the divided parts of the piezoelectric transducer 203 in the eighth embodiment emit ultrasonic beams for scanning purposes. If the permanent magnet 202 did not rotate in this example, data would be acquired only on eight beam spots emitted by the eight divided parts of the piezoelectric transducer 203. But when the transducer components rotate as shown, the ultrasonic beams are moved to scan the object ahead in a cylindrical manner, whereby an ultrasonic sectional view of that object is obtained.

Figure 24:
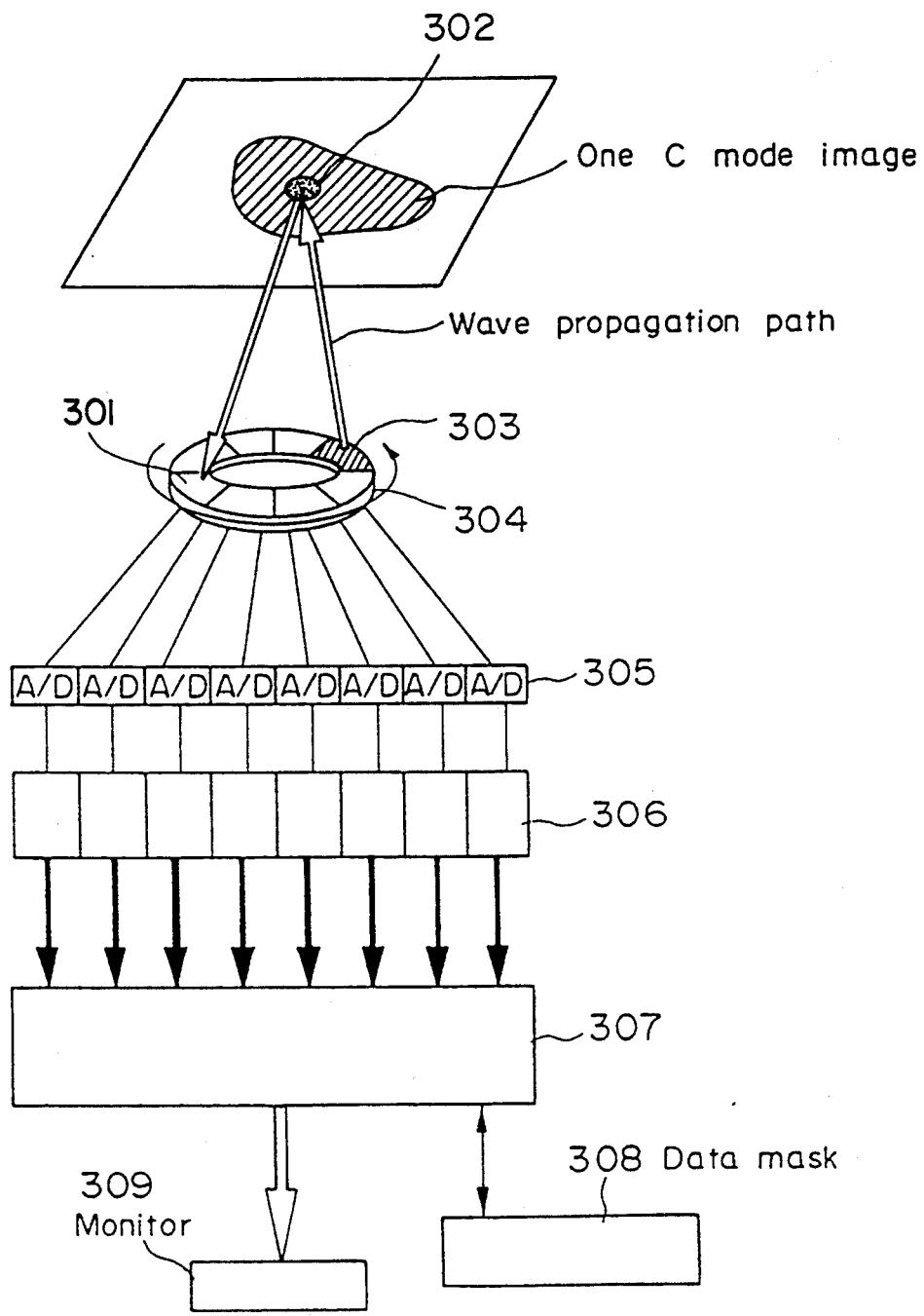
FIG. 24 is a view portraying how a piezoelectric transducer attached to the front end of a cylindrical permanent magnet typically operates.

The scheme under which a piezoelectric transducer such as the transducer 203 of the eighth embodiment is rotated to gain three-dimensional ultrasonic information about the object ahead is disclosed in detail in Japanese Patent Application No. HEI/1-118872. The gist of the disclosure is described below. FIG. 24 portrays how eight elements of a piezoelectric transducer 304 are attached in a donut shape to the front end of a cylindrical permanent magnet and how they are rotated around the center axis of the donut to acquire a three-dimensional ultrasonic image of a target object.

Of the eight elements making up the piezoelectric transducer 304, one element 303 is a transmitting element and the remaining seven are receiving elements 301. In operation, the transmitting element 303 emits spherical waves in pulses. The reflected waves from the object 302 under examination are received by the seven receiving elements 301.

The output from each of the receiving elements 301 is converted from analog to digital format by an A/D converter 305. The digital signal is placed in a wave memory 306. Before the data placed in the wave memory 306 from the receiving elements 301 are used to reconstitute a three-dimensional image of the target object, a data mask 308 needs to be created. That is, in a space to be reconstituted, a plurality of planes (C mode image planes) are first selected in parallel with the plane on which the elements of the piezoelectric transducer 304 are disposed. Then for each C mode image, the time required for the spherical waves to travel from the transmitting element to the target object and back to the receiving element is calculated with each receiving element. The time data are used to create the data mask 308.

For each receiving element 301 keyed to one C mode image, the wave data regarding the image and equal to the previously calculated data mask 308 are retrieved from the wave memory 306. In turn, measuring points are designated based on the result of the total sum added up by an arithmetic processing circuit 307. These points when designated determine a single C mode image for each receiving element 301.

The last two steps above are repeated rapidly to reconstitute the respective C mode images. These C mode images are displayed on a monitor 309 in voxel format or in a manner having gradation codes and pixel magnitude suitably varied. This provides a three-dimensional image of the object located in front of the ultrasonic emitting plane.

Figure 25:
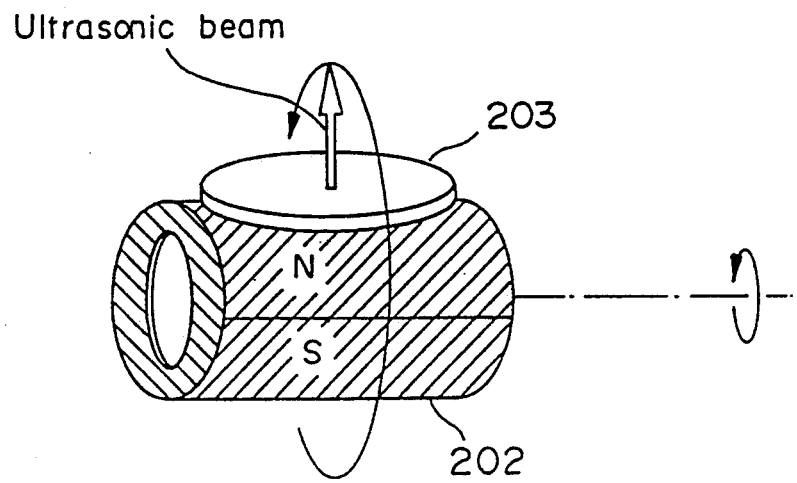
FIG. 25 is a view depicting how a ninth embodiment of the invention performs its ultrasonic scanning.

How the ninth embodiment works will now be described with reference to FIG. 25. FIG. 25 depicts a cylindrical permanent magnet 202 equipped on its outer surface with a piezoelectric transducer 203 in the ninth embodiment. As the permanent magnet 202 rotates, the piezoelectric transducer 203 executes a circumferential scan around it. This provides an ultrasonic sectional image perpendicular to the rotating axis of the permanent magnet 202.

Figure 26:
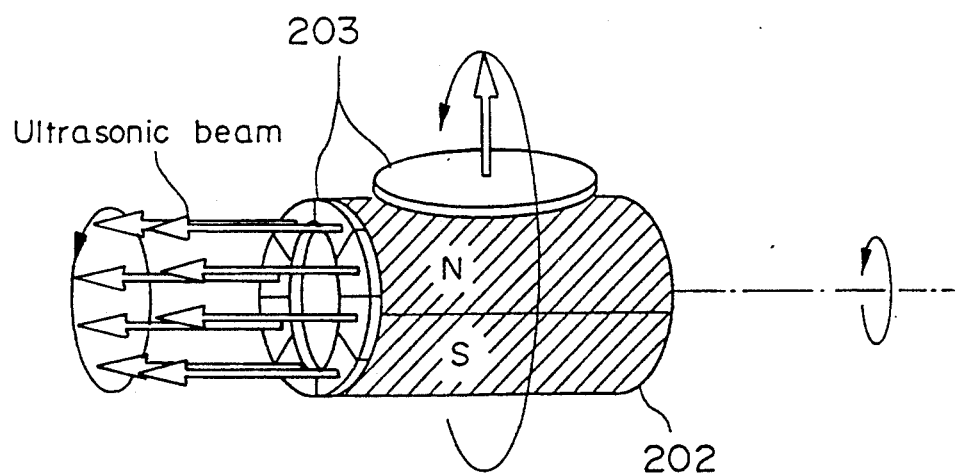
FIG. 26 is a view showing how a tenth embodiment of the invention performs its ultrasonic scanning.

How the tenth embodiment works will now be described with reference to FIG. 26. FIG. 26 shows a combination of the eighth and the ninth embodiments constituting the tenth embodiment. As illustrated, this embodiment scans objects both ahead and around it. That is, a sectional image of the object ahead and a sectional image perpendicular to the rotating shaft of the permanent magnet 202 are available.

Figure 27:
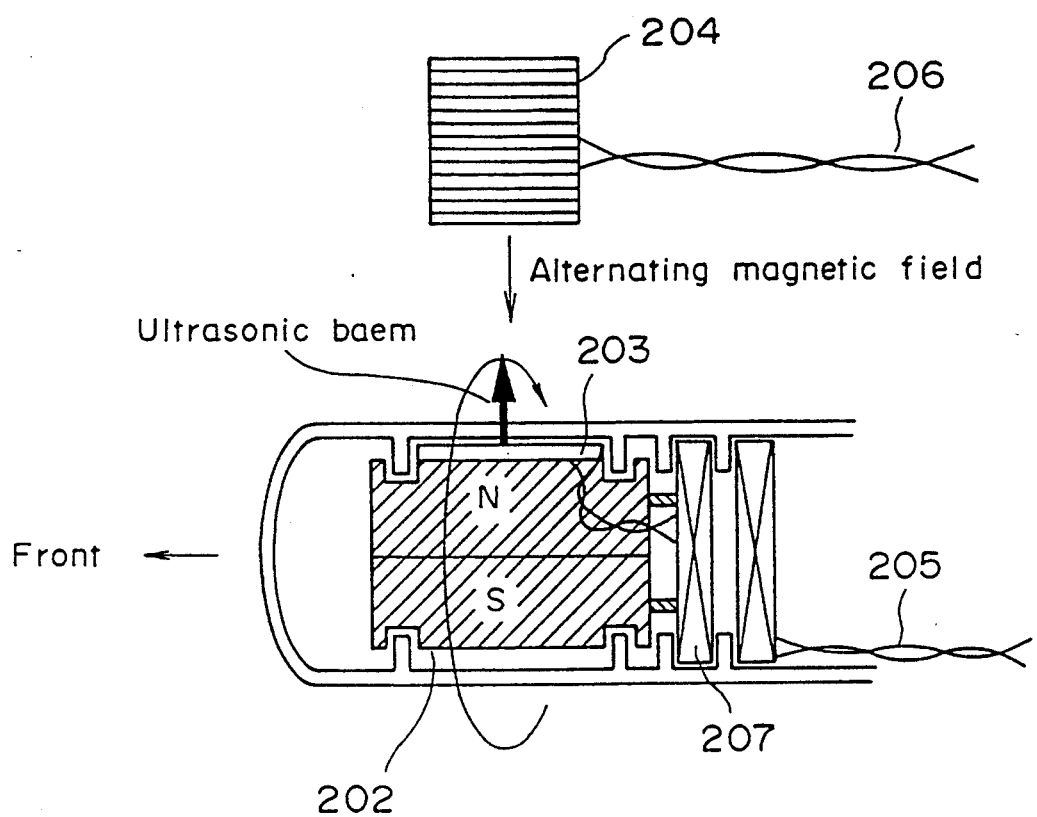
FIG. 27 is a view illustrating how a piezoelectric transducer is powered by use of a rotary transformer in connection with the invention.

FIG. 27 illustrates how the lead wires 205 are extended from the piezoelectric transducer 203 through a rotary transformer 207. In this setup, the rotary transformer 207 mechanically disconnects the lead wires 205 while keeping their electrical connection so that the wires will not be entangled when the permanent magnet 202 rotates. Alternatively, electrical signals may be exchanged by use of a contact brush.

Although not discussed above explicitly, the invention may be practiced using various known techniques. One such technique is the so-called acoustic lens for focusing ultrasonic beams. Other known techniques include piezoelectric transducer attachments such as a matching layer and a backing for efficiency enhancement and frequency band expansion in terms of ultrasonic transmission and reception. The piezoelectric transducer may be an array type or an annular type.

Figure 28:
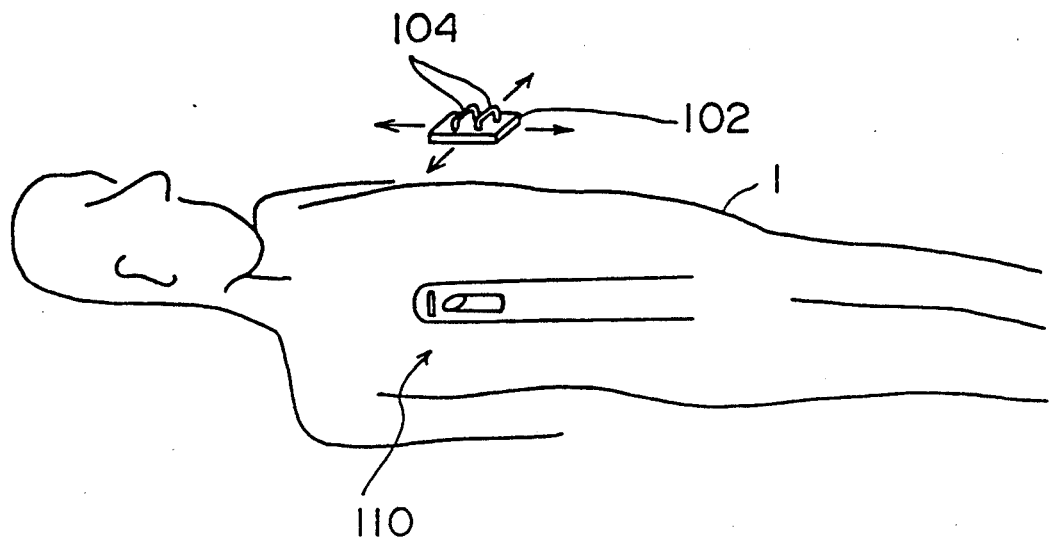
FIG. 28 is an external view of a stator of the invention as it is placed onto the patient.

FIG. 28 is an external view of a stator as it is placed onto a patient. As depicted, an ultrasonic probe 110 is inserted in the patient 1 first, followed by the stator 102 positioned outside the patient's body and opposite to the ultrasonic probe 110. When the stator 102 is equipped with a handle 104, the attachment improves the operability of the stator 102.

Figure 29:
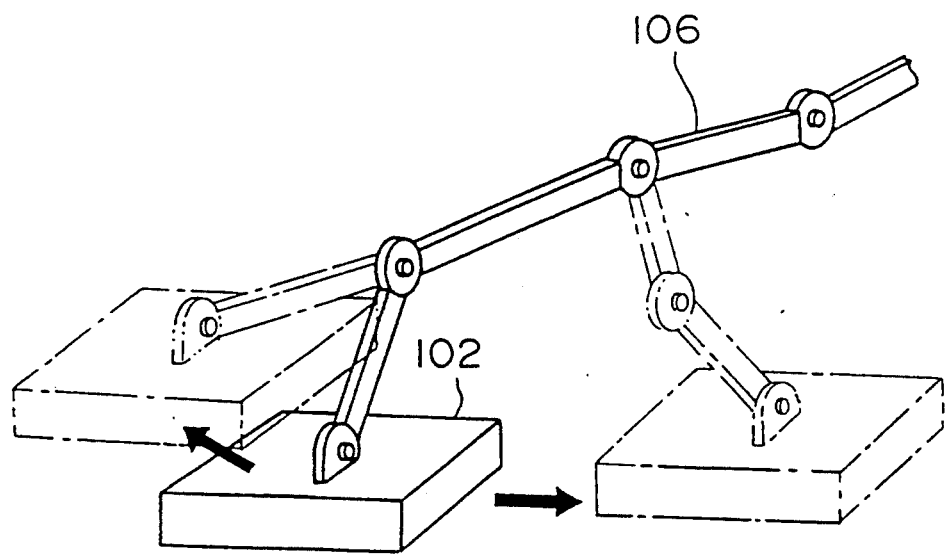
FIG. 29 is an external view of another stator.

FIG. 29 is an external view of another stator. As indicated, an articulated arm 106 is attached to the stator 102. The arm 106 allows the stator 102 to be moved to and fixed in whatever position desired outside the patient's body. This arrangement further enhances the operability of the stator 102. One end of the arm 106 is secured illustratively to the diagnostic system 10 (see FIG. 35) or to the edge of the bed on which the patient lies down.

Figure 30:
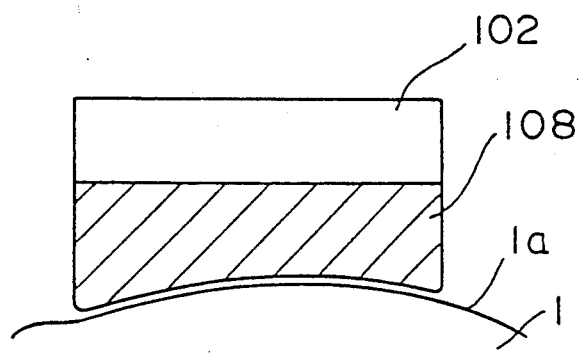
FIG. 30 is a schematic view of still another stator.

FIG. 30 is an external view of another stator. This stator 102 has a soft body 108 such as a piece of rubber attached to its side that comes into contact with the body surface 1a of the patient 1. The soft body 108 gives the patient a soft sense of contact and protects him from any accidental injury that could be caused by the stator 102 during its maneuver.

Figure 31:
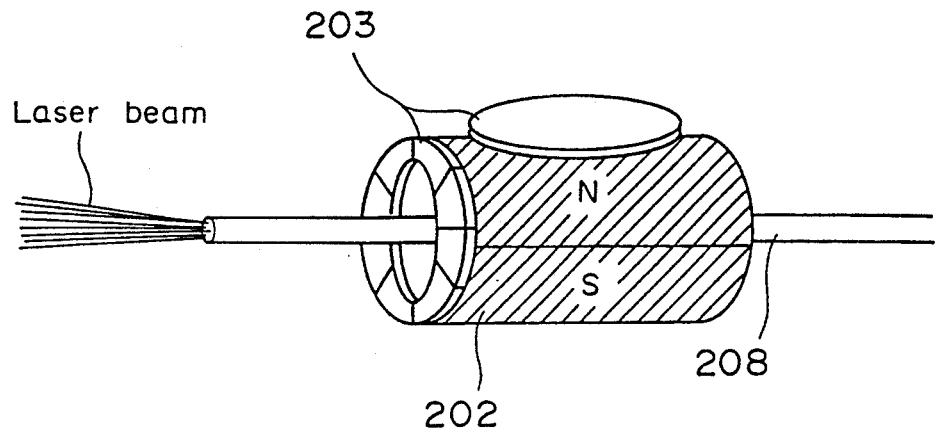
FIG. 31 is a view illustrating how a laser fiber is passed through a hollow permanent magnet.
Figure 32:
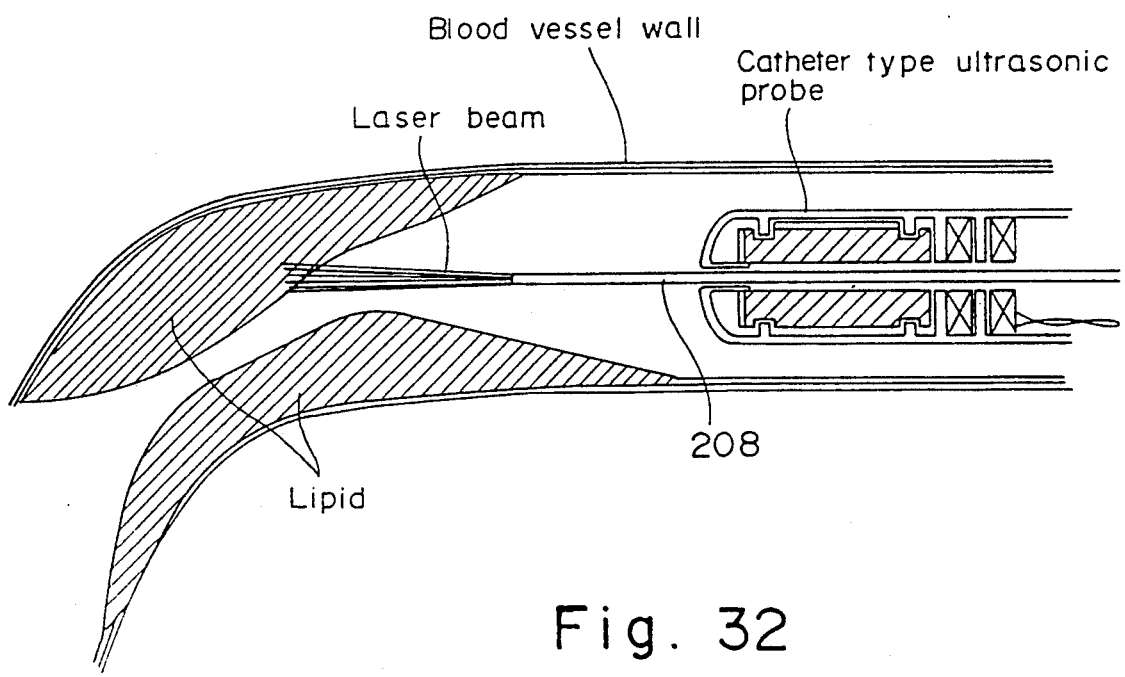
FIG. 32 is a view depicting how the affected part is treated by laser beam while that part is being diagnosed simultaneously by use of an ultrasonic probe.
Figure 33:
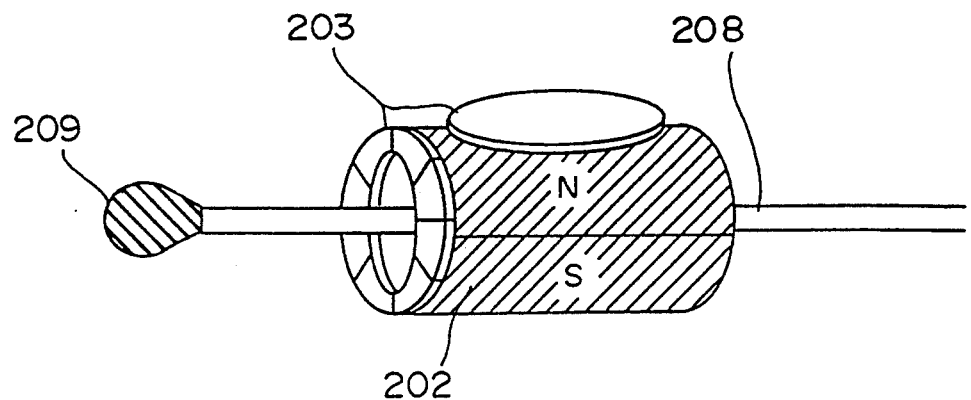
FIG. 33 is a view portraying how a laser fiber tipped with a hot chip is passed through a hollow permanent magnet.
Figure 34:
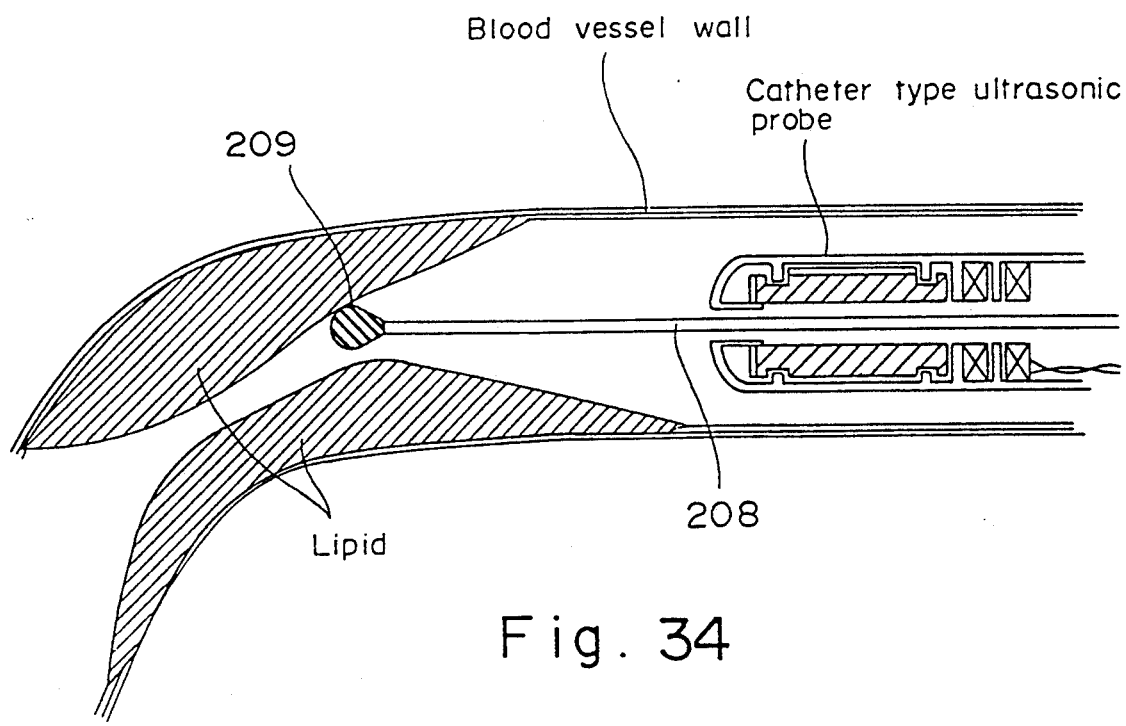
FIG. 34 is a view illustrating how the affected part is treated by a hot chip while that part is being diagnosed simultaneously by use of an ultrasonic probe.
Figure 35:
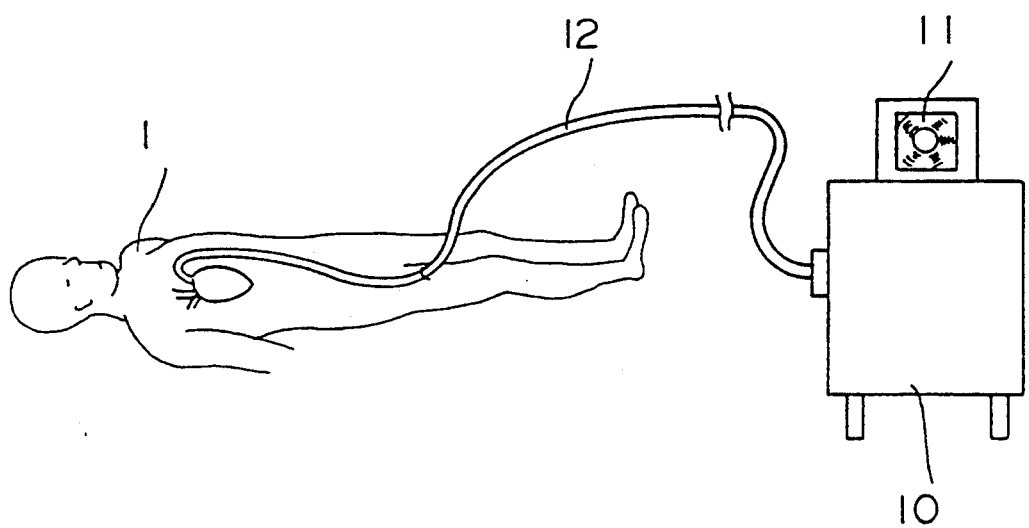
FIG. 35 is a schematic view showing how an ultrasonic probe is inserted illustratively into blood vessels of the living body.
Figure 36:
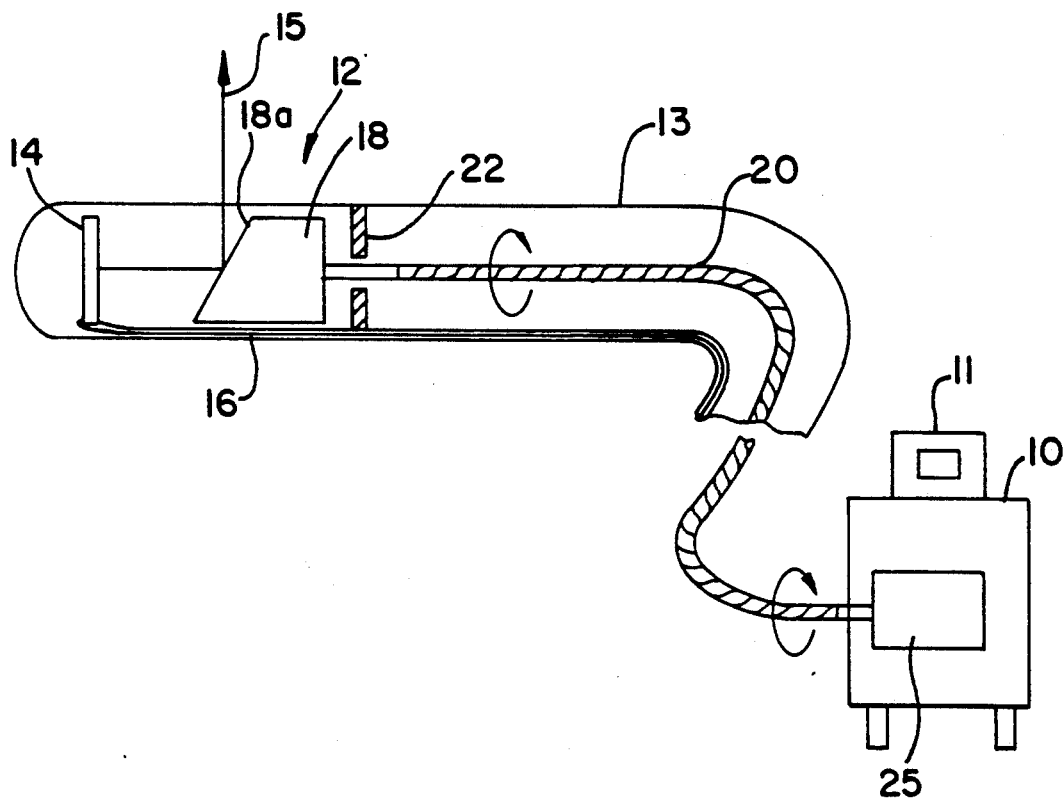
FIG. 36 is a schematic view of a prior art ultrasonic probe.
Figure 37:
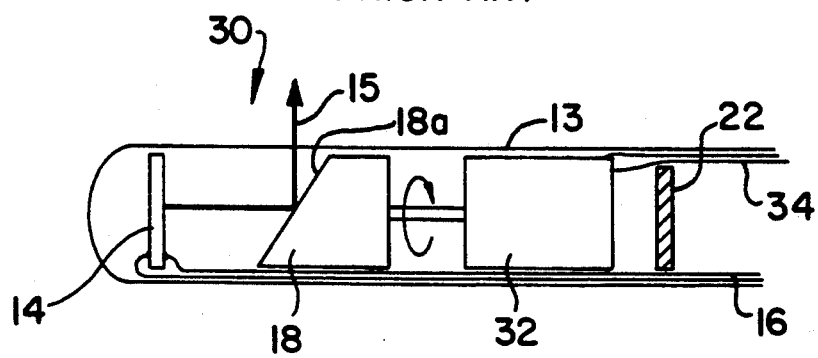
FIG. 37 is a schematic view of another prior art ultrasonic probe.
Figure 38:
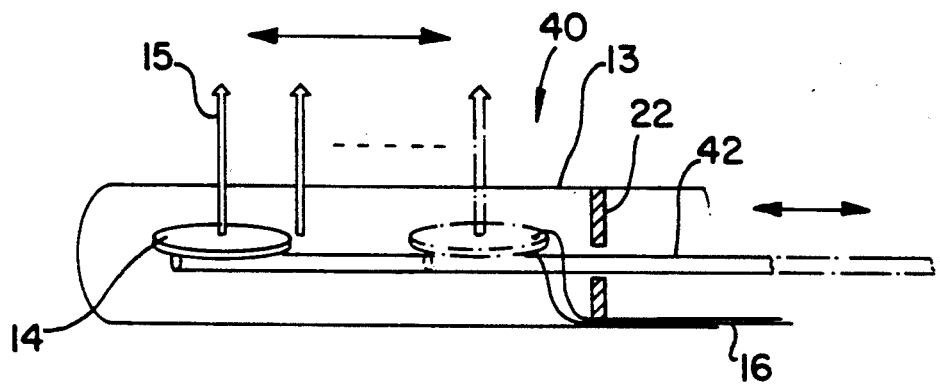
FIG. 38 is a schematic view of another prior art ultrasonic probe.
Figure 39:
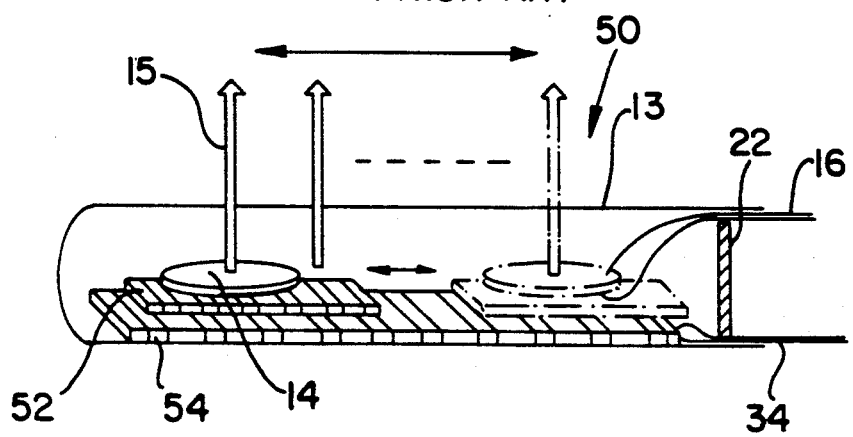
FIG. 39 is a schematic view of another prior art ultrasonic probe.

Below is a description of how the patient's affected part is treated while that part is being diagnosed simultaneously by use of an ultrasonic probe according to the invention. FIG. 31 illustrates how a laser fiber 208 is passed through a hollow permanent magnet 202 so that the affected part is treated by a laser beam from the tip of the laser fiber 208. FIG. 32 depicts how a lipid portion in a blood vessel is removed by a laser beam while that part is being diagnosed simultaneously by use of an ultrasonic probe. FIG. 33 portrays how the laser fiber 208 tipped with a hot chip 209 is passed through the hollow permanent magnet 202. FIG. 34 sketches how the lipid portion in the blood vessel is removed by the hot chip 209 while that portion is being diagnosed simultaneously by use of the ultrasonic probe.

With the eighth embodiment, as described, it is possible to grasp the length of the lipid portion in the blood vessel by diagnosing the objects ahead. However, the inability to diagnose cross sections perpendicular to the rotating axis of the probe makes it impossible with the eighth embodiment to know the thickness of the lipid portion. With the ninth embodiment, the thickness of the lipid portion in the blood vessel is known by diagnosing cross sections perpendicular to the rotating axis of the probe. But without the capability to diagnose objects ahead, the ninth embodiment cannot grasp the length of the lipid portion in the blood vessel.

The tenth embodiment, combining the features of the eighth and the ninth embodiments, makes it possible to diagnose both objects ahead and cross sections perpendicular to the rotating axis of the probe. Thus the length and thickness of the lipid portion in the blood vessel are known at the same time. With the eighth through the tenth embodiments, a laser fiber or a hot tip attached to the end of a laser fiber may be passed through a hollow cylindrical permanent magnet for simultaneous diagnosis and treatment.

With these embodiments, the catheter type ultrasonic probe is inserted in the patient's body safely and unfailingly without the use of an X-ray monitor, and diagnosis and treatment are carried out at the same time. Because the irradiation of the laser beam to the affected part and the movement of the probe are monitored simultaneously, there are drastic reductions in the number of cases where blood vessels are ruptured accidentally by the laser beam or where normal blood vessel tissues are burned inadvertently by the hot chip.

In the eighth through the tenth embodiments, the permanent magnet 202 is a two-pole type and there is only one coil 204. Alternatively, the number of poles may be increased for the permanent magnet and a plurality of coils may be provided. The number of divided elements of the piezoelectric transducer 203 in front of the permanent magnet 202 may be arbitrary as long as there are at least two elements. These elements may be arranged in diverse forms including a double-donut shape. And as described, the invention may be combined with known techniques to improve the acoustic characteristics of ultrasonic waves emitted and received by the piezoelectric transducer 203. Such known techniques include a backing, a matching layer and a lens attached to the piezoelectric transducer. It will also occur to those skilled in the art that a rotary encoder or a non-contact laser-based encoder is used to detect the direction, position and angle of ultrasonic beams emitted and received, and that optimum ultrasonic sectional images are obtained with the diagnostic system utilizing suitable processing and control circuits for processing and controlling both ultrasonic received signals and position signals appropriately.

As many apparently different embodiments of this invention may be made without departing from the spirit and scope thereof, it is to be understood that the invention is not limited to the specific embodiments thereof except as defined in the appended claims.

What is claimed is:

1. An ultrasonic probe comprising:
   a tube extending in a predetermined direction for insertion into an object under examination;
   a transmitter-receiver disposed in said tube so that at least a part thereof is capable of at least one of two movements, one movement being in said predetermined direction, the other movement being rotary around an axis coinciding with said predetermined direction, said transmitter-receiver transmitting ultrasonic waves into said object and receiving the waves reflected back by said object;
   a rotor mounted in said tube for causing at least part of said transmitter-receiver to perform at least one of said two movements; and a stator located outside said object for driving said rotor.

2. An ultrasonic probe according to claim 1, wherein at least a part of said rotor is comprised of by any one of a magnetic substance and a permanent magnet.

3. An ultrasonic probe according to claim 2, wherein said transmitter-receiver includes a piezoelectric transducer, said rotor being located at the backside of said piezoelectric transducer.

4. An ultrasonic probe according to claim 3, wherein said piezoelectric transducer is attached to a front of said rotor and positioned on an extension of the rotating axis of said rotor.

5. An ultrasonic probe according to claim 3, wherein said piezoelectric transducer is attached to a lateral portion of said rotor in respect of the rotating axis of said rotor.

6. An ultrasonic probe according to claim 3, wherein said rotor is shaped in the form of a cylinder.

7. An ultrasonic probe according to claim 2, wherein said transmitter-receiver comprises a piezoelectric transducer and a reflector, said piezoelectric transducer emitting and receiving ultrasonic waves, said reflector reflecting the ultrasonic waves emitted by said piezoelectric transducer outside of said tube, said reflector further reflecting the reflected ultrasonic waves from outside said tube toward said piezoelectric transducer, said reflector containing any one of a magnetic substance and a permanent magnet as said rotor.

8. An ultrasonic probe according to claim 7, wherein the tip of said tube is provided with a hollow chamber filled with an acoustic coupling substance, and wherein said reflector equipped with said rotor is inserted in said chamber, the entrance to said chamber being capped with said piezoelectric transducer.

9. An ultrasonic probe according to claim 7, wherein the tip of said tube is provided with a hollow chamber, the deep end of said chamber being capped with said piezoelectric transducer, the space inside said chamber being filled with an acoustic coupling substance, the tip end of said chamber being provided with said reflector having said rotor, the tip of said chamber being closed with a cap.

10. An ultrasonic probe according to claim 1, wherein said stator has a handle.

11. An ultrasonic probe according to claim 1, wherein said stator is attached to an articulated arm mechanism.

12. An ultrasonic probe according to claim 1, wherein the surface of said stator which comes into contact with said object under examination has is comprised of a soft material.

13. An ultrasonic probe according to claim 1, wherein said transmitter-receiver includes a first piezoelectric transducer attached to an end of said rotor and a second piezoelectric transducer attached to a side of said rotor.

* * * * *

UNITED STATES PATENT AND TRADEMARK OFFICE
CERTIFICATE OF CORRECTION

PATENT NO. : 5,313,950
DATED : May 24, 1994
INVENTOR(S) : Hiroshi ISHIKAWA et al.

It is certified that error appears in the above-identified patent and that said Letters Patent is hereby corrected as shown below:

Column 4,    line 47, change "b, and c" to --B and C--;

line 50, change "A,B and D" to --A-D--.

Column 14,   line 14, delete "by";

line 61, delete "has".

Signed and Sealed this

Twenty-seventh Day of September, 1994

Attest:

BRUCE LEHMAN

*Attesting Officer*    *Commissioner of Patents and Trademarks*